(12) United States Patent
Hoshino et al.

(10) Patent No.: US 9,173,943 B2
(45) Date of Patent: Nov. 3, 2015

(54) IMPRINTED POLYMER NANOPARTICLES

(75) Inventors: Yu Hoshino, Irvine, CA (US); Kenneth J. Shea, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 819 days.

(21) Appl. No.: 13/144,027

(22) PCT Filed: Jan. 11, 2010

(86) PCT No.: PCT/US2010/020624
§ 371 (c)(1),
(2), (4) Date: Dec. 2, 2011

(87) PCT Pub. No.: WO2010/081076
PCT Pub. Date: Jul. 15, 2010

(65) Prior Publication Data
US 2012/0097613 A1   Apr. 26, 2012

Related U.S. Application Data

(60) Provisional application No. 61/143,924, filed on Jan. 12, 2009.

(51) Int. Cl.
| | |
|---|---|
| *A61K 47/32* | (2006.01) |
| *A61K 47/36* | (2006.01) |
| *A61K 47/42* | (2006.01) |
| *C08F 2/10* | (2006.01) |
| *C08F 2/44* | (2006.01) |
| *A61K 9/51* | (2006.01) |
| *B01D 15/38* | (2006.01) |
| *B01J 20/26* | (2006.01) |
| *B01J 20/28* | (2006.01) |
| *B82Y 5/00* | (2011.01) |
| *B82Y 30/00* | (2011.01) |
| *C07K 1/22* | (2006.01) |
| *G01N 33/543* | (2006.01) |

(52) U.S. Cl.
CPC ............ *A61K 47/32* (2013.01); *A61K 9/5138* (2013.01); *A61K 9/5192* (2013.01); *A61K 47/36* (2013.01); *A61K 47/42* (2013.01); *B01D 15/3852* (2013.01); *B01J 20/261* (2013.01); *B01J 20/267* (2013.01); *B01J 20/268* (2013.01); *B01J 20/28007* (2013.01); *B82Y 5/00* (2013.01); *B82Y 30/00* (2013.01); *C07K 1/22* (2013.01); *C08F 2/10* (2013.01); *C08F 2/44* (2013.01); *G01N 33/5432* (2013.01); *G01N 33/54346* (2013.01); *G01N 2600/00* (2013.01)

(58) Field of Classification Search
CPC ....... A61K 47/32; A61K 47/42; A61K 47/36; C08F 2/10; C08F 2/44
USPC .......... 525/54.1; 530/402, 415; 524/849, 850, 524/853
See application file for complete search history.

(56) References Cited

U.S. PATENT DOCUMENTS

| | | | | |
|---|---|---|---|---|
| 5,317,097 | A | * | 5/1994 | Miller et al. ................ 536/24.31 |
| 6,117,681 | A | * | 9/2000 | Salmons et al. ............. 435/456 |
| 6,127,154 | A | | 10/2000 | Mosbach et al. |
| 6,936,421 | B2 | * | 8/2005 | Anderson et al. .............. 506/10 |
| 2004/0058006 | A1 | * | 3/2004 | Barry et al. .................. 424/489 |
| 2004/0063159 | A1 | | 4/2004 | Mosbach et al. |
| 2005/0130163 | A1 | | 6/2005 | Smith et al. |
| 2005/0224452 | A1 | | 10/2005 | Spiess et al. |
| 2008/0003363 | A1 | | 1/2008 | Park et al. |
| 2008/0241963 | A1 | | 10/2008 | Lin et al. |

FOREIGN PATENT DOCUMENTS

| | | |
|---|---|---|
| WO | WO 94/11403 | 5/1994 |
| WO | WO 99/19276 | 4/1999 |
| WO | WO 00/41723 | 7/2000 |
| WO | WO 02/02647 | 1/2002 |
| WO | WO 02/068958 | 9/2002 |
| WO | WO 2009/085016 | 7/2009 |

OTHER PUBLICATIONS

Ko, D.Y., et al.; Macromolecular Rapid Communications, 2006, vol. 27, p. 1367-1372.*
Hoshino, Y., et al.; Journal of the American Chemical Society, 2008, vol. 130, p. 15242-15243.*
Hoshino, Y., et al.; Journal of the American Chemical Society, 2008, Supporting Information, p. S1-S5.*
Extended European Search Report for EP Application No. 10729617.0, dated Jun. 20, 2012.
Britt, A. M., Burkhart, K. K. & Billingsley, M. L. "Reversal of toxicity using avidin-based hemoperfusion: A model system in rats using biotinylated melittin." Pharmacology. 50, 307-312 (1995).
Duncan, R. "The dawning era of polymer therapeutics," Nat Rev Drug Discov, 2, 347-360 (2003).
Grunigen, R. V. & Schneider, C. H. "Antigenic structure of the hexacosapeptide melittin: evidence for three determinants, one with a helical conformation." Immunology 66, 339-342 (1989).
Hansen, E. D. "Recent developments in the molecular imprinting of proteins" Biomaterials 28, 4178-4191 (2007).

(Continued)

*Primary Examiner* — Robert Jones, Jr.
(74) *Attorney, Agent, or Firm* — Casimir Jones, S.C.

(57) ABSTRACT

The present invention relates to imprinted polymer nanoparticles. In particular, the present invention provides imprinted polymer nanoparticles polymerized in the presence of a target molecule (e.g., peptide), wherein the imprinted polymer nanoparticles comprise vinyl, acryl, and/or methacryl monomers, wherein the monomers have affinity for the target molecule. The present invention also relates to methods of using imprinted polymer nanoparticles in biomacromolecular purification methods (e.g., to purify monoclonal antibodies or hormones), in toxin elimination methods (e.g., hemoperfusion), in diagnostics, in research, as well as in therapeutic methods (e.g., therapeutic methods where antisera or monoclonal antibodies are normally employed).

12 Claims, 6 Drawing Sheets

(56) References Cited

OTHER PUBLICATIONS

Hart, B. R. & Shea, K. J. "Synthetic peptide receptors: molecularly imprinted polymers for the recognition of peptides using peptide-metal interactions." J. Am. Chem. Soc. 123, 2072-2073 (2001).

Li, Y. Yang, H. H. You, Q. H. Zhuang, Z. X. & Wang, X. R. "Protein recognition via surface molecularly imprinted polymer nanowires." Anal. Chem. 78, 317-320 (2006).

Mosbach, K. "The promise of molecular imprinting," Scientific American 295, 86-91 (2006).

Nishino, H, Huang, C.-S. & Shea, K. J. "Selective Protein Capture by Epitope Imprinting," Angew. Chem. Int. Ed. 2006, 45, 2392-2396.

Rachkov, A. Minoura, N. & Shimizu, T. "Peptide separation using molecularly imprinted polymer prepared by epitope approach" Anal. Sci. 17, 609-612 (2001).

Rothenfluh DA., Bermudez, H., O'Neil, C. P. & Hubbell, J. A. "Biofunctional polymer nanoparticles for intra-articular targeting and retention in cartilage" Nature Mater. 7, 248-254 (2008).

Sigma Aldrich Product Catalog—Acrylic Monomers, www.sigmaaldrich.com/materials-science/material-science-products.html?TablePage=16397884 Retrieved Aug. 1, 2011.

Sigma Aldrich Product Catalog—Allyl Monomers, www.sigmaaldrich.com/materials-science/material-science-products.html?TablePage=20203440 Retrieved on Aug. 1, 2011.

Sigma Aldrich Product Catalog—Vinyl Esters, www.sigmaaldrich.com/materials-science/material-science-products.html?TablePage=16371054 Retrieved on Aug. 1, 2011.

Sigma Aldrich Product Catalog—Vinyl Ethers, www.sigmaaldrich.com/materials-science/material-science-products.html?TablePage=16371064 Retrieved on Aug. 1, 2011.

Tan, C. J. & Tong, Y. W. "The effect of protein structural conformation on nanoparticle molecular imprinting of ribonuclease A using miniemulsion polymerization," Langmuir. 23, 2722-2730 (2007).

Wulff, G. & Sarhan, A. "Use of polymers with enzyme-analogous structures for the resolution of racemates," Angew. Chem. Int. Edn. Engl. 11, 341-343 (1972).

Yan, M. & Ramstrom, O. "Molecularly imprinted materials, science and technology" (Marcel Dekker, 2005).

International Search Report and Written Opinion for Int'l Application No. PCT/US2010/020624, dated Sep. 27, 2010.

* cited by examiner a b c

IMPRINTED POLYMER NANOPARTICLES

CROSS-REFERENCE TO RELATED APPLICATION

The present application claims priority to U.S. Provisional application Ser. No. 61/143,924, filed Jan. 12, 2009, which is herein incorporated by reference in its entirety.

FIELD OF THE INVENTION

The present invention relates to imprinted polymer nanoparticles. In particular, the present invention provides imprinted polymer nanoparticles polymerized in the presence of a target molecule (e.g., peptide), wherein the imprinted polymer nanoparticles comprise vinyl, acryl, and/or methacryl monomers, wherein the monomers have affinity for the target molecule. The present invention also relates to methods of using imprinted polymer nanoparticles in biomacromolecular purification methods (e.g., to purify monoclonal antibodies or hormones), in toxin elimination methods (e.g., hemoperfusion), in diagnostics, in research, as well as in therapeutic methods (e.g., therapeutic methods where antisera or monoclonal antibodies are normally employed).

BACKGROUND OF THE INVENTION

Antibodies are large polypeptide complexes (IgG; 150 kDa (~10 nm)-IgM; 900 kDa (~40 nm)) used by the immune system to identify and neutralize foreign objects such as bacteria, viruses and toxins in blood or other bodily fluids of vertebrates (FIG. 2c). To neutralize specific antigens in a heterogeneous mixture they recognize specific molecules or fragments of molecules and bind to them with high affinity. Because of their compact size they can diffuse into most parts of the body through blood, tissue fluids and mucus[5, 16]. Since the first discovery of antibody-mediated immunotherapy over a hundred years ago, antibodies are now widely used as tools in medicine and research[1-3]. Despite their enormous importance antibodies cannot be employed under all conditions. As proteins their effectiveness can be diminished by extremes in pH, enzymes, temperature and environment (non-aqueous solvents, denaturants)[17].

Antibodies are of undisputed importance to research and medicine. Research applications currently include flow cytometry, protein separation and identification, and examining protein expression. When antibodies for a particular epitope, or target protein, aren't available, researchers may need to synthesize their own. There is also a need to produce pure, safe antibodies on a larger scale for use as therapeutics. A new trend is that antibodies are being prescribed for chronic conditions and are given in relatively high, concentrated doses (grams instead of mg) due to their lower potency than other therapeutics. A recent 2007 paper reported that 20% of biopharmaceuticals in clinical trials are monoclonal antibodies, and uses for the diagnosis and treatment of cancer, treatment of rheumatoid arthritis, multiple sclerosis, and psoriasis, prevention of transplant rejection, as use as a prophylactic, have already been approved. In order to meet this demand, purification capacity will need to expand almost 30% each year.

As costs associated with cell culture and harvesting antibodies have decreased, the purification steps, particularly the protein A purification, have come to account for a larger percentage of the expenses associated with antibody production and thus have greater optimization potential. The affinity separation step has been pinpointed by many researchers as a bottleneck in the production process. With current methods, antibodies are produced in cell bioreactors and harvested from cell culture supernatant, then purified via affinity separation before undergoing viral inactivation at low pH, polishing, viral filtration, and the final concentration step. Affinity separation is the primary capture step, and protein A is the most commonly used reagent for the initial antibody capture. These methods are expensive and time consuming.

What is needed are methods for preparing target specific nanoparticles that are stable, less-expensive to manufacture, and that do not rely on harsh conditions such that non-denatured target molecules can be imprinted.

SUMMARY OF THE INVENTION

The present invention relates to imprinted polymer nanoparticles. In particular, the present invention provides imprinted polymer nanoparticles polymerized in the presence of a target molecule (e.g., peptide), wherein the imprinted polymer nanoparticles comprise vinyl, acryl, and/or methacryl monomers, wherein the monomers have affinity for the target molecule. The present invention also relates to methods of using imprinted polymer nanoparticles in biomacromolecular purification methods (e.g., to purify monoclonal antibodies or hormones), in toxin elimination methods (e.g., hemoperfusion), in diagnostics, in research, as well as in therapeutic methods (e.g., therapeutic methods where antisera or monoclonal antibodies are normally employed).

In certain embodiments, the present invention provides compositions comprising imprinted polymer nanoparticles that are specific for a target molecule, wherein the imprinted polymer nanoparticle comprise vinyl, acryl, and/or methacryl monomers, and wherein the monomers have affinity for the target molecule.

In certain embodiments, the imprinted polymer nanoparticles result from polymerization of the monomers in the presence of the target molecule. In other embodiments, the composition further comprises the target molecule (e.g., a low percentage of residual target molecule, such as 0.01 percent of the composition). In particular embodiments, 30-50% of the imprinted polymer nanoparticle is either the vinyl monomers, or the acryl monomers, or the methacryl monomers. In other embodiments, 0-10% of the imprinted polymer nanoparticle is either the vinyl monomers, or the acryl monomers, or the methacryl monomers. In certain embodiments, all three monomers are part of the imprinted polymer nanoparticles. In some embodiments, two of the monomers are part of the imprinted polymer nanoparticles.

In particular embodiments, the imprinted polymer nanoparticle comprises at least two of the monomers, wherein the at least two monomers are selected from: N-t-butylacrylamide (TBAm), acrylic acid (AAc), N-isopropylacrylamide (NIPAm), N,N'-methylenebis(acrylamide) (MBAm), N,N'-ethylenebis(acrylamide) (EBAm), acrylamide (AAm), 1-vinyl imidazole (VI), N-(3-aminopropyl)acrylamide (APAm), N-phenyl acrylamide (PAm), N-[2-[[[5-(Dimethylamino)-1-naphthalenyl]sulfonyl]-aminolethyl1-2-propenamide (DANSAm), fluorescein o-acrylate (FAc), polyethylene grycol diacrylate (PEGDAc), N-t-butylmethacrylamide (TBMAm), methacrylic acid (MAAc), N-isopropylmethacrylamide (NIPMAm), N,N'-methylenebis(methacrylamide) (MBMAm), N,N'-ethylenebis(methacrylamide) (EBMAm), methacrylamide (MAAm), N-(3-aminopropyl)methacrylamide (APMAm), N-phenyl methacrylamide (PMAmN-[2-[[[5-(Dimethylamino)-1-naphthalenyl]sulfonyl]-amino]ethyl]-2-methyl-Z-propenamide (DANSMAm), fluorescein o-methacrylate (FMAc) and polyethylene grycol dimethacrylate (PEGDMAc). In certain embodiments, TBAm=about 40 mol %, AAc=about 5 mol %, NIPAm=about 53 mol % and MBAm=about 2 mol %. Other momomers may be used with the present invention and are known in the art. Examples of such monomers are found at the following web sites that all start with "www." and continue:
"sigmaaldrich.com/materials-science/material-science-products.html?TablePage=16397884"
"sigmaaldrich.com/materials-science/material-science-products.html?TablePage=20203440"
"sigmaaldrich.com/materials-science/material-science-products.html?TablePage=16371054"
"sigmaaldrich.com/materials-science/material-science-products.html?TablePage=16371064"

In further embodiments, the imprinted polymer nanoparticles further comprises a crosslinking agent. In some embodiments, the crosslinking agent comprises N,N'-methylenebis(acrylamide) or similar reagent.

In additional embodiments, the present invention provides methods of making imprinted polymer nanoparticles comprising: a) providing: i) vinyl, acryl, and/or methacryl monomers, ii) target molecules, and iii) an aqueous medium; and b) combining the monomers and the target molecules in the aqueous medium to generate a reaction mixture; and c) incubating the reaction mixture under polymerization conditions such that imprinted polymer nanoparticles are generated that are specific for the target molecules.

In certain embodiments, the target molecules are proteins. In other embodiments, the target molecules are toxins. In further embodiments, the target molecules are polysaccharides. In some embodiments, the reaction mixture further comprises a surfactant. In further embodiments, the surfactant comprises sodium dodecyl sulfate. In particular embodiments, the reaction mixture further comprises a crosslinking agent. In further embodiments, the crosslinking agent comprises N,N'-methylenebis(acrylamide). In some embodiments, the reaction mixture further comprises acrylamide and/or acrylic acid. In particular embodiments, the polymerization conditions comprise bubbling nitrogen through the reaction mixture. In additional embodiments, the reaction mixture further comprises ammonium persulfate. In some embodiments, the reaction mixture further comprises N,N,N',N'-tetramethylethylenediamine. In other embodiments, the polymerization conditions comprises a temperature between 20 degrees Celsius and 26 degrees Celsius. In certain embodiments, the polymerization conditions comprises dialyzing the reaction mixture against excess water at least twice per day for 3 to 5 days. In further embodiments, the monomers are dissolved in an organic solvent before addition to the reaction mixture. In some embodiments, the aqueous medium comprises water. In particular embodiments, the combining and the incubating is under conditions such that the target molecule is not denatured.

In some embodiments, the present invention provides methods of purifying target molecules from an initial sample, comprising: a) providing; i) an initial sample comprising target molecules and contaminating molecules, and ii) imprinted polymer nanoparticles that are specific for the target molecules, wherein the imprinted polymer nanoparticle comprise vinyl, acryl, and/or methacryl monomers, wherein the monomers have affinity for the target molecules; and b) contacting the initial sample with the imprinted polymer nanoparticles under conditions such that at least a portion of the contaminating molecules are removed from the initial sample thereby generating a purified target molecule sample.

In particular embodiments, the target molecules are antibodies or antibody fragments. In other embodiments, the antibodies are monoclonal antibodies or antibody fragments. In some embodiments, the target molecules are antibodies, and the imprinted nanoparticles are specific for the Fc region of the antibodies. In further embodiments, the target molecule is a therapeutic protein. In other embodiments, the imprinted nanoparticles are operably linked to a solid support. In further embodiments, the solid support is inside a column.

In some embodiments, the present invention provides articles of manufacture comprising: a) a purification device comprising a solid support; and b) imprinted polymer nanoparticles that are specific for a target molecule, wherein the imprinted polymer nanoparticle comprise vinyl, acryl, and/or methacryl monomers, wherein the monomers have affinity for the target molecule, and wherein the imprinted nanoparticles are operably linked to the solid support.

In other embodiments, the purification device is a purification column. In further embodiments, the purification device is a hemoperfusion cartridge or similar device. In some embodiments, the solid support comprises a resin. In other embodiments, the target molecule is an antibody or antibody fragment.

In some embodiments, the present invention provides methods of performing hemoperfusion comprising: a) providing; i) a subject comprising contaminated blood, wherein the contaminated blood comprises target contaminant molecules, and ii) imprinted polymer nanoparticles that are specific for target molecules, wherein the imprinted polymer nanoparticle comprise vinyl, acryl, and/or methacryl monomers, and wherein the monomers have affinity for the target molecules; and b) withdrawing at least a portion of the contaminated blood from the subject; c) contacting the contaminated blood with the imprinted nanoparticles under conditions such that at least a portion of the target contaminant molecules are removed from the contaminated blood thereby generating purified blood; and d) returning at least a portion of the purified blood to the patient.

In particular embodiments, the present invention provides methods of treating a subject comprising: a) providing; i) a subject suffering from one or more symptoms of a disease, and ii) a therapeutic formulation comprising imprinted polymer nanoparticles specific for a target molecule, wherein the imprinted nanoparticles each imprinted polymer nanoparticles comprise vinyl, acryl, and/or methacryl monomers, wherein the monomers have affinity for the target molecule, and b) administering the therapeutic formulation to the subject under conditions such that at least one of the symptoms is reduced or eliminated. In some embodiments, the target molecule is selected from the group consisting of: CD20, TNF-a, Her-2, and VEGF, EGFR.

In certain embodiments, the present invention provides therapeutic formulations comprising: a) imprinted polymer nanoparticles that are specific for a target molecule, wherein the imprinted polymer nanoparticle comprise vinyl, acryl, and/or methacryl monomers, wherein the monomers have affinity for the target molecule, and b) a physiological tolerable liquid.

In additional embodiments, the present invention provides therapeutic formulations comprising: a) imprinted polymer nanoparticles that are specific for a target molecule, wherein the imprinted polymer nanoparticle comprise vinyl, acryl, and/or methacryl monomers, wherein the monomers have affinity for the target molecule, and b) a therapeutic agent useful for treating a disease, wherein the target molecule is involved with the pathogenesis of the disease.

In certain embodiments, the present invention provides compositions comprising an imprinted nanoparticle comprising: at least two components selected from: N-t-butylacrylamide (TBAm), acrylic acid (AAc), N-isopropylacrylamide (NIPAm), N,N'-methylenebis(acrylamide) (MBAm), N,N'-ethylenebis(acrylamide) (EBAm), acrylamide (AAm), 1-vinyl imidazole (VI), N-(3-aminopropyl)acrylamide (APAm), N-phenyl acrylamide (PAm), N-[2-[[[5-(Dimethylamino)-1-naphthalenyl]sulfonyl]-aminolethyl1-2-propenamide (DANSAm), fluorescein o-acrylate (FAc), polyethylene grycol diacrylate (PEGDAc), N-t-butylmethacrylamide (TBMAm), methacrylic acid (MAAc), N-isopropylmethacrylamide (NIPMAm), N,N'-methylenebis(methacrylamide) (MBMAm), N,N'-ethylenebis(methacrylamide) (EBMAm), methacrylamide (MAAm), N-(3-aminopropyl)methacrylamide (APMAm), N-phenyl methacrylamide (PMAmN-[2-[[[5-(Dimethylamino)-1-naphthalenyl]sulfonyl]-amino]ethyl]-2-methyl-Z-propenamide (DANSMAm), fluorescein o-methacrylate (FMAc) and polyethylene grycol dimethacrylate (PEGDMAc). In certain embodiments, TBAm=about 40 mol %, AAc=about 5 mol %, NIPAm=about 53 mol % and MBAm=about 2 mol %. In certain embodiments, TBAm=about 30-80 mol % (e.g., 30, 31, 32, 33, 34, 35, 36, 37, 38, 39, 40, 41, 42, 43, 44, 45, 46, 47, 48, 49, 50 . . . 60 . . . 70 . . . 80 mol %). In some embodiments, AAc=about 0.1-70 mol % (e.g., 0 . . . 10 . . . 25 . . . 35, 36, 37, 38, 39, 40, 41, 42, 43, 44, 45, 46, 47, 48, 49, 50, 51, 52, 53, 54, 55, 56, 57, 58, 59, 60 . . . 70 mol %) and NIPAm=0-70 mol % (e.g., 0 . . . 10 . . . 25 . . . 35, 36, 37, 38, 39, 40, 41, 42, 43, 44, 45, 46, 47, 48, 49, 50 . . . 60 . . . 70 mol %).

In some embodiments, the present invention provides methods of making imprinted nanoparticles comprising: a) providing: i) N-isopropylacrylamide (NIPAm) monomers, ii) N-tert-butylacrylamide (TBAm) monomers, iii) target molecules, and iv) an aqueous medium; and b) combining the NIPAm monomers, the TBAm monomers, and the target molecules in the aqueous medium under polymerization conditions such that imprinted nanoparticles are generated that are specific for said target molecules.

In particular embodiments, the present invention provides methods of making imprinted nanoparticles comprising: a) providing: i) N-isopropylacrylamide (NIPAm) monomers, ii) N-tert-butylacrylamide (TBAm) monomers, iii) target molecules, and iv) an aqueous medium; and b) combining the NIPAm monomers, the TBAm monomers, and the target molecules in the aqueous medium to generate a reaction mixture; and c) incubating the reaction mixture under polymerization conditions such that imprinted nanoparticles are generated that are specific for the target molecules. In particular embodiments, no organic solvent is employed. In other embodiments, no heating step is employed.

In certain embodiments, 30-50% of the reaction mixture is the TBAm monomers. In other embodiments, the target molecules are polypeptides. In further embodiments, the target molecules are toxins. In other embodiments, the target molecules are polysaccharides or any other biological or non-biological molecule that is known.

In further embodiments, the reaction mixture further comprises an ionic surfactant. In some embodiments, the ionic surfactant comprises sodium dodecyl sulfate or similar composition. In particular embodiments, the reaction mixture further comprises a crosslinking agent. In certain embodiments, the crosslinking agent comprises N,N'-methylenebis (acrylamide) or similar agent. In other embodiments, the reaction mixture further comprises acrylamide. In particular embodiments, the reaction mixture further comprises acrylic acid. In further embodiments, the polymerization conditions comprise deoxidization. In certain embodiments, the deoxidization comprises bubbling nitrogen through the reaction mixture. In certain embodiments, the reaction mixture further comprises radical initiator. In certain embodiments, the radical initiator comprises ammonium persulfate. In some embodiments, the reaction mixture further comprises catalyst. In certain embodiments, the catalyst is N,N,N',N'-tetramethylethylenediamine.

In particular embodiments, the polymerization conditions comprises an ambient temperature. In certain embodiments, the ambient temperature is between 0-15 degrees Celsius and 5-30 degrees Celsius. In further embodiments the temperature is about 25 degree Celsius. In other embodiments, the polymerization conditions comprises dialyzing the reaction mixture against excess water at least twice per day for 3 to 5 days. In some embodiments, the monomers are dissolved in an organic solvent before addition to the reaction mixture. In other embodiments, the aqueous medium comprises water. In particular embodiments, the present invention provides methods of generating target imprinted nanoparticles comprising: a) providing: i) N-isopropylacrylamide (NIPAm) monomers, ii) N-tert-butylacrylamide (TBAm) monomers, iii) acrylic acid, iv) acrylamide, v) an ionic surfactant, vi) an aqueous medium, vii) a crosslinking agent, and viii) a target molecule; and b) combining the NIPAm monomers, the TBAm monomers, the acrylic acid, the acrylamide, the ionic surfactant, the crosslinking agent and the target molecules in the aqueous medium to generate a reaction mixture; and c) incubating the reaction mixture under polymerization conditions such that imprinted nanoparticles are generated that are specific for the target molecule.

In some embodiments, the present invention provides composition comprising an imprinted nanoparticle specific for a target molecule, wherein the imprinted target molecule comprises N-isopropylacrylamide (NIPAm) monomers and N-tert-butylacrylamide (TBAm) monomers.

In other embodiments, the present invention provides compositions comprising: i) a target molecule, and ii) an imprinted target molecule specific for the target molecule, wherein the imprinted target molecule comprises N-isopropylacrylamide (NIPAm) monomers and N-tert-butylacrylamide (TBAm) monomers, and wherein the imprinted target molecule is bound to the target molecule.

In certain embodiments, the present invention provides compositions comprising an imprinted nanoparticle comprising: a) N-isopropylacrylamide (NIPAm), and b) at least one additional component selected from: acrylamide (AAm), acrylic acid (AAc), vinyl imidazole (VI), N-t-butylacrylamide (TBAm), wherein the formula (NIPAm, 98-(W+X+Y+Z) mol %) describes the makeup of said said imprinted nanoparticle, and wherein W=AAm mol %, X=AAc mol %, Y=VI mol %, and Z=TBAm mol %. In certain embodiments, W=0%, X=about 5%, Y=0%, and Z=about 40%, and therefore NIPAm=about 53%. In certain embodiments, W=about 0-15% (e.g., 0, 1, 2, 3, 4, 5, 6, 7, 8, 9, 10, 11, 12, 13, 14, or 15%). In some embodiments, X=about 0-15% (e.g., 0, 1, 2, 3, 4, 5, 6, 7, 8, 9, 10, 11, 12, 13, 14, or 15%). In particular embodiments, Y=about 0-15% (e.g., 0, 1, 2, 3, 4, 5, 6, 7, 8, 9, 10, 11, 12, 13, 14, or 15%). In some embodiments, Z=about 0-70% (e.g., 0 . . . 10 . . . 25 . . . 35, 36, 37, 38, 39, 40, 41, 42, 43, 44, 45, 46, 47, 48, 49, 50, 51, 52, 53, 54, 55, 56, 57, 58, 59, 60 . . . 70%).

In certain embodiments, the present invention provides compositions comprising an imprinted nanoparticle comprising: a) N-isopropylacrylamide (NIPAm), and b) at least one additional component selected from: acrylamide (AAm), acrylic acid (AAc), N-(3-aminopropyl)methacrylamide hydrochloride (APM), N-t-butylacrylamide (TBAm), wherein the formula (NIPAm, 98-(W+X+Y+Z) mol %) describes the makeup of said said imprinted nanoparticle, and wherein W=AAm mol %, X=AAc mol %, Y=APM mol %, and Z=TBAm mol %. In certain embodiments, W=0%, X=about 5%, Y=0%, and Z=about 40%, and therefore NIPAm=about 53%. In certain embodiments, W=about 0-15% (e.g., 0, 1, 2, 3, 4, 5, 6, 7, 8, 9, 10, 11, 12, 13, 14, or 15%). In some embodiments, X=about 0-15% (e.g., 0, 1, 2, 3, 4, 5, 6, 7, 8, 9, 10, 11, 12, 13, 14, or 15%). In particular embodiments, Y=about 0-15% (e.g., 0, 1, 2, 3, 4, 5, 6, 7, 8, 9, 10, 11, 12, 13, 14, or 15%). In some embodiments, Z=about 0-70% (e.g., 0 . . . 10 . . . 25 . . . 35, 36, 37, 38, 39, 40, 41, 42, 43, 44, 45, 46, 47, 48, 49, 50, 51, 52, 53, 54, 55, 56, 57, 58, 59, 60 . . . 70%).

In certain embodiments, the present invention provides methods of purifying target molecules from an initial sample, comprising: a) providing; i) an initial sample comprising target molecules and contaminating molecules, and ii) imprinted nanoparticles specific for the target molecule, wherein the imprinted nanoparticles each comprise N-isopropylacrylamide (NIPAm) monomers and N-tert-butylacrylamide (TBAm) monomers; and b) contacting the initial sample with the imprinted nanoparticles under conditions such that at least a portion of the contaminating molecules are removed from the initial sample thereby generating a purified target molecule sample.

In certain embodiments, the target molecules are antibodies or antibody fragments (e.g., polyclonal, monoclonal, Fab fragments, etc.). In certain embodiments, the antibodies are monoclonal antibodies (e.g., HERCEPTIN, RITUXAN, REMICADE, AVASTIN, HUMIRA, ERBITUX, etc.) or antibody fragments. In particular embodiments, the target molecules are antibodies, and the imprinted nanoparticles are specific for the Fc region of the antibodies. In other embodiments, the target molecule is a therapeutic protein (e.g., EPO). In further embodiments, the target molecule is a cytokine or small molecule. In particular embodiments, the imprinted nanoparticles are operably linked to a solid support (e.g., there the solid support is within a column).

In some embodiments, the present invention provides articles of manufacture comprising: a) a purification device comprising a solid support; and b) imprinted nanoparticles specific for a target molecule, wherein the imprinted nanoparticles comprise N-isopropylacrylamide (NIPAm) monomers and N-tert-butylacrylamide (TBAm) monomers, wherein the imprinted nanoparticles are operably linked to the solid support.

In particular embodiments, the purification device is a purification column or similar device. In further embodiments, the purification device is a hemoperfusion cartridge or other device used in hemoperfusion containing an adsorbent. In certain embodiments, the solid support comprises a resin. In further embodiments, the target molecule is an antibody or antibody fragment.

In some embodiments, the present invention provides methods of performing hemoperfusion comprising: a) providing; i) a subject comprising contaminated blood, wherein the contaminated blood comprises target contaminant molecules, and ii) imprinted nanoparticles specific for the target contaminant molecules, wherein the imprinted nanoparticles each comprise N-isopropylacrylamide (NIPAm) monomers and N-tert-butylacrylamide (TBAm) monomers; and b) withdrawing at least a portion of the contaminated blood from the subject; b) contacting the contaminated blood with the imprinted nanoparticles under conditions such that at least a portion of the target contaminant molecules are removed from the contaminated blood thereby generating purified blood; and c) returning at least a portion of the purified blood to the patient.

In particular embodiments, the present invention provides methods of treating a subject comprising: a) providing; i) a subject suffering from one or more symptoms of a disease, and ii) a therapeutic formulation comprising imprinted nanoparticles specific for a target molecule, wherein the imprinted nanoparticles each comprise N-isopropylacrylamide (NIPAm) monomers and N-tert-butylacrylamide (TBAm) monomers; and b) administering the therapeutic formulation to the subject under conditions such that at least one of the symptoms is reduced or eliminated. In some embodiments, the target molecule is selected from the group consisting of: CD20, TNF-a, Her-2, and VEGF, EGFR.

In certain embodiments, the present invention provides therapeutic formulations comprising: a) imprinted nanoparticles specific for a target molecule, wherein the imprinted nanoparticles comprise N-isopropylacrylamide (NIPAm) monomers and N-tert-butylacrylamide (TBAm) monomers, and b) a physiological tolerable liquid (e.g., buffer).

In some embodiments, the present invention provides therapeutic formulations comprising: a) imprinted nanoparticles specific for a target molecule, wherein the imprinted nanoparticles each comprise N-isopropylacrylamide (NIPAm) monomers and N-tert-butylacrylamide (TBAm) monomers, and b) a therapeutic agent useful for treating a disease, wherein the target molecule is involved with the pathogenesis of the disease.

DESCRIPTION OF THE INVENTION

Figure 1:
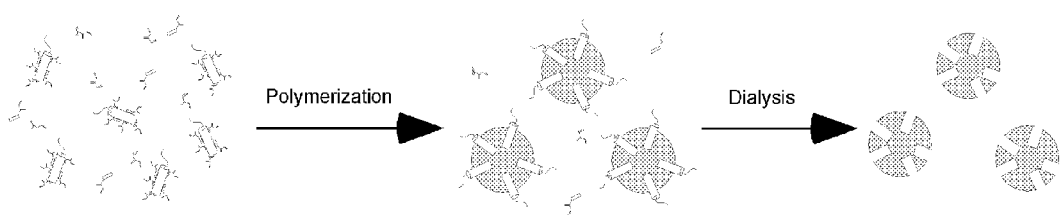
FIG. 1a shows a scheme illustrating the preparation of melittin imprinted NPs.
FIG. 1b shows examples of various monomers employed.
FIG. 1c shows an amino acid sequence of melittin.
Figure 1:
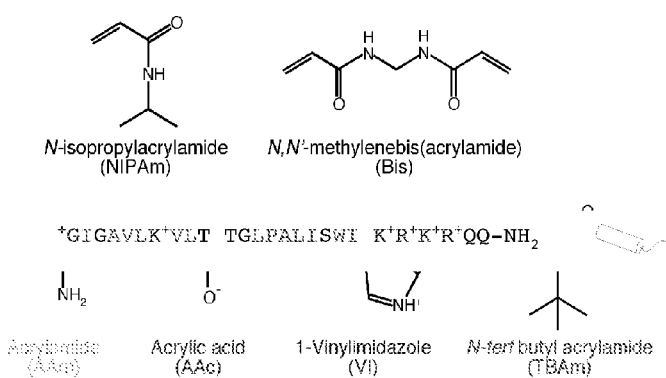

The present invention relates to imprinted polymer nanoparticles. In particular, the present invention provides imprinted polymer nanoparticles polymerized in the presence of a target molecule (e.g., peptide), wherein the imprinted polymer nanoparticles comprise vinyl, acryl, and/or methacryl monomers, wherein the monomers have affinity for the target molecule. The present invention also relates to methods of using imprinted polymer nanoparticles in biomacromolecular purification methods (e.g., to purify monoclonal antibodies or hormones), in toxin elimination methods (e.g., hemoperfusion), in diagnostics, in research, as well as in therapeutic methods (e.g., therapeutic methods where antisera or monoclonal antibodies are normally employed).

Synthetic polymer nanoparticles (NPs) capable of recognizing specific biomacromolecules and neutralizing their activity are of significant interest as substitutes for antibodies. Such particles can be utilized as inexpensive and stable functional materials for applications including disease therapy, antidotes for toxins and microbicides for viruses and bacteria as well as drug targeting[1-5]. Molecular imprinting creates populations of specific recognition sites in polymers by polymerization of monomers in the presence of a target (imprint) molecule[6-8]. The method has been most successful for small molecules. Recently, efforts to extend this approach to prepare synthetic receptors for biomacromolecules have meet with some success[9-14]. The present invention provides for the synthesis of molecular imprinted nanoparticles (NPs) with a size, neutralization capacity and affinity similar to that of natural antibodies[15]. It is believed that the present invention is the first example of a polymer NP that recognizes a biomacromolecule by itself without conjugation with ligands and neutralizes its activity in vitro and in vivo[4, 5].

i. Target Molecules

The present invention is not limited by the type of target molecule that the imprinted nanoparticles will bind to. Exemplary binding molecules include, but are not limited to, tumor marker (e.g., CD20, HER2/neu receptor), hormones (e.g., TNF-a, VEGF, IL6, insuline), receptors of hormones (e.g., IL6 receptor) exotoxins (e.g., staphylococcal enterotoxin B, PVL, PMSα peptides, α-hemolysin, anthrax neurotoxins and botulinum neurotoxins), endotoxins (e.g., LPS), envelope proteins of pathogenic viruses (e.g., envelope proteins of HIV, HHV, influenzavirus and hepatitis viruses), antibodies and fragment of antibodies.

ii. Protein Purification

Laboratories can produce a large amount of identical polypeptides. These polypeptides are used for research, diagnostics, food or therapeutics. The significant cost of producing polypeptides is in separating them from other proteins and contaminants. For example, in order for monoclonal antibodies, which is one of the biggest polypeptide products, to use therapeutically without side effects, they must be highly pure. After researchers identify an antibody and the isolation process, the largest cost of producing antibodies is in separating them from other proteins and contaminants in the liquid harvested. The imprinted polymer nanoparticles of the present invention address this need by providing particles that are capable of specifically binding to antibodies (e.g., a conserved region of variety of antibodies), capturing them for clinical or research use, or any other type of use.

The conventional method for the isolation of proteins from a mixture is by passing the mixture (e.g., from animal serum or cell culture) through a column (e.g., glass tube) packed with Protein A or Protein G-coupled beads. Both Protein A and G are bacterial cell components which naturally bind to most classes of human antibodies. Once the antibody is bound to these proteins in the column and the unwanted proteins have flowed through, a series of washes releases the purified antibodies from the column. The imprinted nanoparticles of the present invention (e.g., directed toward antibody Fc regions) performs the same function as Protein A or Protein G would in the isolation of antibodies.

Although protein purification has made great strides in recent decades, with increased specificity and efficiency, there is still room for improvement. While protein-based capture methods are possible to reuse many times, this would require careful handling, and they do not have the ability to be cleaned at higher pHs. An additional step is often necessary to ensure that none of the toxic Protein A which may have leached out of the columns is able to contaminate the final product. The process of coupling Protein A to the beads is also a challenge for some researchers, and in certain instances, the purification process captures other antibodies in addition to the desired one. The imprinted nanoparticles of the present invention avoid these problems with protein A and similar materials and can be used for monoclonal or polyclonal antibody purification, or for purifying any other type of protein, such as those used in therapeutics.

iii. Toxin Elimination

In particular embodiments, the imprinted nanoparticles of the present invention are used for toxin elimination method such as hemoperfusion. Hemoperfusion is a treatment technique in which large volumes of the patient's blood are passed over an adsorbent substance in order to remove toxic substances from the blood. Adsorption is a process in which molecules or particles of one substance are attracted to the surface of a solid material and held there.

Normally, the sorbents most commonly used in hemoperfusion are resins and various forms of activated carbon or charcoal. However, binding specificity of these materials are relatively poor and sometimes they adsorb important blood factors as well as target molecules. Because binding mechanism of those materials is mostly just hydrophobic interaction. The present invention provides for the use of the imprinted nanoparticles of the present invention as more specific and high affinity sorbents for target molecules.

Hemoperfusion works by pumping the blood drawn through the arterial catheter into a column or cartridge containing the sorbent material. As the blood passes over the carbon or resin particles in the column, the toxic molecules or particles are drawn to the surfaces of the sorbent particles and trapped within the column. The blood flows out the other end of the column and is returned to the patient through the tubing attached to the venous catheter. Hemoperfusion is able to clear toxins from a larger volume of blood than hemodialysis or other filtration methods; it can process over 300 mL of blood per minute.

Hemoperfusion has three major uses major applications including: 1) removing nephrotoxic drugs or poisons from the blood in emergency situations; 2) removing waste products from the blood in patients with kidney disease; and 3) providing supportive treatment before and after transplantation for patients in liver failure. The imprinted nanoparticles of the present invention may be used for these, and other, applications. In some embodiments, hemoperfusion with the imprinted nanoparticles of the present invention is used to treat overdoses of barbiturates, meprobamate, glutethimide, theophylline, digitalis, carbamazepine, methotrexate, ethchlorvynol, and acetaminophen, as well as treating paraquat poisoning.

A hemoperfusion system can be used with or without a hemodialysis machine. In general, after the patient has been made comfortable, two catheters are placed in the arm, one in an artery and one in a nearby vein. After the catheters have been checked for accurate placement, the catheter in the artery is connected to tubing leading into the hemoperfusion system, and the catheter in the vein is connected to tubing leading from the system through a pressure monitor. The patient is given heparin at the beginning of the procedure and at 15-20-minute intervals throughout the hemoperfusion in order to prevent the blood from clotting. The patient's blood pressure is also taken regularly. A typical hemoperfusion treatment takes about three hours.

iv. Therapeutic Formulations and Applications

The imprinted nanoparticles of the present invention are useful for treating a subject having a pathology or condition that is amenable to treatment with target molecule binding molecules (e.g., diseases that are treated with monoclonal antibodies). The imprinted nanoparticles of the present invention may be administered by any suitable means, including parenteral, subcutaneous, orally, topical, intraperitoneal, intrapulmonary, and intranasal, and, intralesional administration (e.g. for local immunosuppressive treatment). Parenteral infusions include, but are not limited to, intramuscular, intravenous, intraarterial, intraperitoneal, or subcutaneous administration. In addition, imprinted nanoparticles are suitably administered by pulse infusion, particularly with declining doses. Preferably, the dosing is given by injections, most preferably intravenous or subcutaneous injections, depending in part on whether the administration is brief or chronic. It is noted that unlike most protein therapeutics, the imprinted nanoparticles, in certain embodiments, may be administered orally (e.g., they are not destroyed by the digestive system).

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the imprinted nanoparticles of the present invention are generally dependent on (a) the unique characteristics of the active compound and the particular therapeutic or prophylactic effect to be achieved, and (b) the limitations inherent in the art of compounding such an active compound for the treatment of sensitivity in individuals. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The imprinted nanoparticles of the invention can be incorporated into pharmaceutical compositions suitable for administration to a subject. For example, the pharmaceutical composition may comprises imprinted nanoparticles and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the imprinted nanoparticles.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson. ed., Marcel Dekker, Inc., New York, 1978.

In certain embodiments, the imprinted nanoparticles of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, imprinted nanoparticles of the invention are coformulated with and/or coadministered with one or more additional therapeutic agents.

The pharmaceutical compositions of the invention may include a "therapeutically effective amount" or a "prophylactically effective amount" of the imprinted nanoparticles of the invention. A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the imprinted nanoparticle to elicit a desired response in the individual. A therapeutically effective amount is also one in which any toxic or detrimental effects of the imprinted nanoparticle are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); Xg (time gravity); and C (degrees Centigrade).

Example 1

Preparation and Use of Imprinted Nanoparticles

This example describes the preparation and characterization of imprinted nanoparticles.

Methods

Preparation of NPs

Non imprinted nanoparticles (NIP NPs) were synthesized as follows. N-isopropylacrylamide (NIPAm, 98−(W+X+Y+Z) mol %), N,N'-methylenebisacrylamide (MBAM 2 mol %), acrylamide (AAm, W mol %), acrylic acid (AAc, X mol %), vinyl imidazole (VI, Y mol %), N-tert-butylacrylamide (TBAm, Z mol %) and sodium dodecyl sulfate (SDS, 10 mg) were dissolved in water (50 mL) and the resulting solutions were filtered through a no. 2 Whatman paper filter. TBAm (Z mol %) was dissolved in 1 mL of ethanol before addition to the monomer solution, resulting in a total monomer concentration of 6.5 mM. Nitrogen was bubbled through the reaction mixture for 30 min. Following the addition ammonium persulfate (30 mg) and N,N,N',N'-tetramethylethylenediamine (15 µl), the polymerization was carried out at 23-25° C. for 15-20 hours under a nitrogen atmosphere. The NPs were purified by dialysis against pure water (twice a day changes) for >4 days. MIP NPs were synthesized in an identical manor except that 600 nM of melittin was added to polymerization mixture before the filtration step. Synthesized nanoparticles are shown in Table 1 below.

TABLE 1

Yield and diameter of NIP/MIP NPs.

| Functional monomers | Target molecule | Yield (%) | Diameter (nm) |
|---|---|---|---|
| 5% AAc, 40% TBAm | — | 51 | 68 |
| 5% AAm, 0% TBAm | Melittin | 70 | 8.5 |
| 5% AAm, 10% TBAm | Melittin | 81 | 63 |
| 5% AAm, 40% TBAm | Melittin | 64 | 9.1 |
| 5% AAc, 0% TBAm | Melittin | 91 | NA |
| 5% AAc, 10% TBAm | Melittin | 84 | NA |
| 5% AAc, 40% TBAm | Melittin | 79 | 54 |
| 5% AAc, 50% TBAm | Melittin | NA | Aggregated |
| 5% VI, 0% TBAm | Melittin | 27 | 8.0 |
| 5% VI, 10% TBAm | Melittin | 2 | 8.0 |
| 5% VI, 40% TBAm | Melittin | NA | Aggregated |
| 5% AAm&AAc, 0% TBAm | Melittin | 81 | 12 |
| 5% AAm&AAc, 10% TBAm | Melittin | 82 | 9.9 |
| 5% AAm&AAc, 40% TBAm | Melittin | 88 | 56 |
| 40% TBAm | Melittin | 90 | 63 |

All NPs were polymerized with 2% MBAM (Bis) and NIPAm. Total monomer concentration was 6.5 mM.

Characterization of NPs

The hydrodynamic diameter of NPs was determined in aqueous solution by dynamic light scattering (DLS) (HORIBA LB-550). The temperature of the NP samples was controlled via Peltier device at 25±0.1° C. Yield of NPs was determined by measuring weight of NP after lyophilization. Apparent molarities of NPs were calculated by the following equation, $$[NPs] = \frac{6}{\pi N_A d^3 \rho} X$$

where $N_A$ is Avogadro's constant, d is average of hydrodynamic diameter of particles, $\rho$ is polymer density of particles and X is polymer concentration (mg ml$^{-1}$). The $\rho$ values for NIPAm based swollen particles were estimated by Ogawa et. al.[19] to be ~0.01 g cm$^{-3}$. The polymer density of deswollen particles were estimated to be $2^3$~$3^3$ times higher than swollen particles (0.08<$\rho$<0.27)[18].

Preparation of Biotinylated Melittin

Biotinylation of melittin was followed by standard procedures[23].

QCM Analysis

An Affinix Q$^4$ QCM instrument (Initium Co. Ltd) with four 500 mL cylindrical cells (10 mm i.d.) equipped with a 27 MHz QCM plate (8 mm diameter quartz plate and 4.9 mm$^2$ Au electrode) at the bottom of the cell in a temperature-controlled system. Avidin, alubumin, fibrinogen and γ-globulines were covalently immobilized on the QCM plate as follows[24]. To the cleaned bare Au electrode, 3,3'-dithiodipropionic acid was immobilized, and then carboxylic acids were activated as N-hydroxysuccinimidyl esters on the surface. Proteins were reacted with the activated esters on the QCM plate. Biotinylated melittin was immobilized on avidin immobilized QCM plates using the biotin-avidin method in 10 mM HEPES buffer, pH 7.4. Interactions between NPs and proteins/melittin were observed in 25±0.1° C. in water with 6.9 µM SDS. The dissociation constant of NPs to melittin was calculated under assumptions that all particles have same affinity to melittin.

Cell Cytotoxicity Inhibition Assay

HT-1080 human fibrosarcoma cells were grown in Dulbecco's Modified Eagle Medium (Wako Chemicals, Osaka, Japan) supplemented with 10% heat-inactivated fetal bovine serum (FBS, Japan Bioserum Inc., Hiroshima, Japan) at 37°

C. in a 5% CO$_2$ atmosphere. HT-1080 cells (1×10$^4$ cells/well) were seeded on a 96-well culture plate (Beckton Dickinson Japan, Tokyo, Japan) and cultured for 24 h. Cells were washed twice with Dulbecco's phosphate buffered saline and treated with 3.0 μM mellitin and various concentrations of NPs (40% TBAm, 5% AAc) in Hanks' Balanced Salted Solution (HBSS) supplemented with 10% FBS for 24 h. After incubation, 10 μl/well of Alamar Blue® (Serotec Ltd, UK) was added. After 4 h incubation, viable cells were determined by fluorescence (Ex/Em=550/590 nm) measured by a fluorescence plate reader (ARVOsx, Perkin Elmer Japan, Tokyo, Japan). The cytotoxicity was calculated as the percentage of control cell viability (non-mellitin exposed cell). KaleidaGraph version 4.0 (Synergy software, Reading, Pa.) was used to calculate the concentrations associated with 50% inhibition of measured parameter (IC$_{50}$) using three-parameters approximation analysis.

In Vivo Assay

BALB/c mice (5 week-old male, 18-25 g) were purchased from Japan SLC (Shizuoka, Japan) and were cared for according to institutional and regulatory guidelines. Various concentration of mellitin was incubated with or without 9.4 mg kg$^{-1}$ of MIP NPs (40% TBAm, 5% AAc) for 30 min in 0.3 M glucose solution and cooled down on ice to dissolve all precipitation then injected into mice slowly via tail vein. The neutralizing effect of NPs against mellitin induced lethality were evaluated by the 24-hour survival rate. A time of 24 h was set as a maximum for mice surviving toxicity. JMP 6.0 (SAS institute inc.) was used for log-rank test of surviving curves. KaleidaGraph version 4.0 (Synergy software, Reading, Pa.) was used to calculate the LD$_{50}$ using two-parameters approximation analysis.

Hemolytic Activity Neutralization Assay

Neutralization of hemolytic activity of mellitin by NPs were assayed by a modified standard hemolytic assay procedure[27]. Red blood cells (RBC) from bovine or mice preserved blood were washed three times with PBS (35 mM phosphate buffer/0.15 M NaCl, pH 7.3) by centrifugation for 10 min at 800 g and resusupended in PBS. Melittin or α-toxin (final concentration in RBC suspension, 1.8 μM) was pre-incubated with NPs for 30 min in 37° C. in PBS. Melittin and NP mixture was then added to 100 μl of a solution of RBC in PBS to reach final volume of 200 μl (final erythrocyte concentration, 3% v/v). The resulting suspension was incubated at 37° C. for 30 min. Samples were then centrifuged at 800 g for 10 min. Release of hemoglobin was monitored by measuring the absorbance (A$_{sample}$) of the supernatant at 415 nm. Controls for zero neutralization and 100% neutralization of hemolytic activity consisted of RBC suspended with 1.8 μM melittin (A$_{0\%}$) and RBC suspension without melittin (A$_{100}$%) respectively. The percentage of neutralization was calculated according to the equation.

$$\text{Neutralization} = \frac{A_{sample} - A_{0\%}}{A_{100\%} - A_{0\%}} \times 100$$

Results/Discussion

This Example identified mild conditions of precipitation polymerization using acrylamides such as N-isopropylacrylamide (NIPAm) as an attractive candidate for generating biomacromolecular imprinted NPs. These formulations have been shown to yield 10-100 nm mono modal polymer NPs in aqueous solution incorporating a number of functional monomers. In addition, nanoparticle formation requires very low concentrations of surfactant[18, 19]. The monomers used for polymer synthesis included NIPAm (98−(W+X+Y+Z) mol %) as the backbone monomer in combination with acrylamide (AAm, W mol %), acrylic acid (AAc, X mol %), vinyl imidazole (VI, Y mol %) and N-t-butylacrylamide (TBAm, Z mol %), as hydrogen-bonding, negative-charged, positive charged and hydrophobic functional monomers respectively. N,N'-methylenebisacrylamide (MBAM, 2 mol %) was used as crosslinker to preserve the 3D structure of the imprinted binding site (FIG. 1b). By employing combinations of the above monomers, this example synthesized a small combinatorial library of co-polymers (see, Table 1). Significantly, this polymer synthesis does not require organic solvent nor a heating step that would be expected to cause denaturation of most of biomacromolecules.

Figure 2:
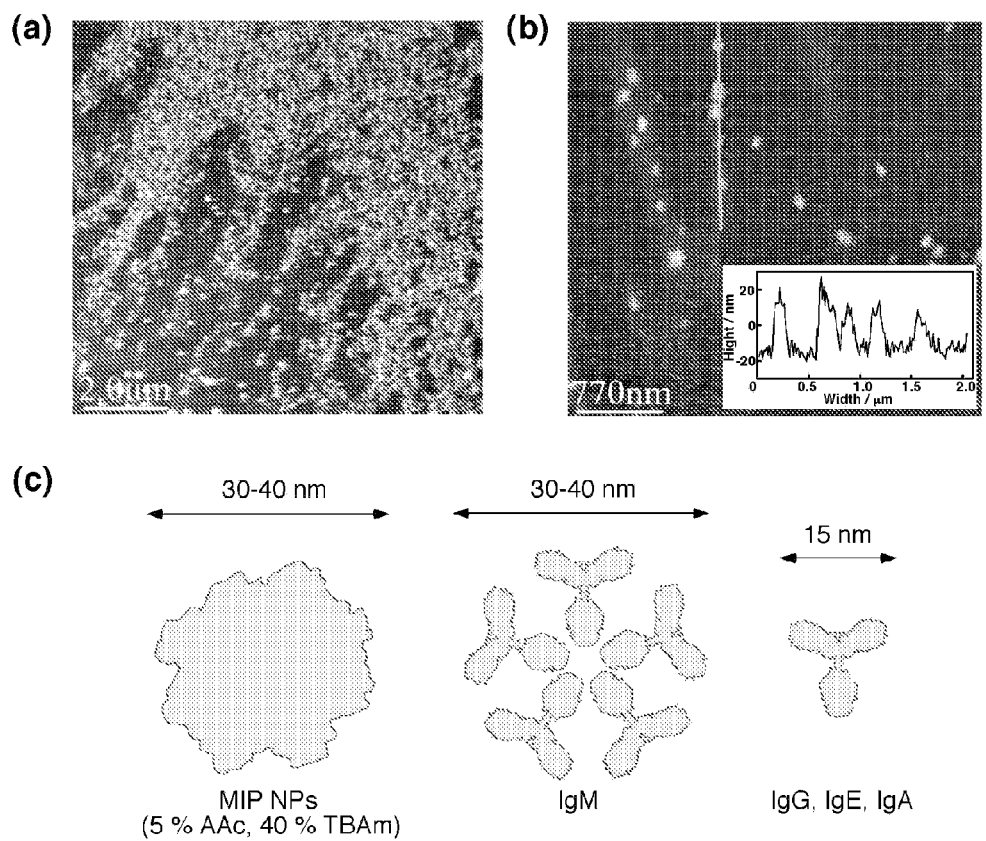
FIGS. 2a-b shows AFM images of melittin imprinted (MIP) NPs synthesized with 5 mol % AAc, 40 mol % TBAm, 2 mol % MBAm and 53 mol % NIPAm. Height profile of cross-section (line in b) is shown in insert.
FIG. 2c shows a comparison of approximate particle size between MIP NPs (5 mol % AAc, 40 mol % TBAm, 2 mol % MBAm and 53 mol % NIPAm), IgM and IgG, IgE, IgA.

Melittin, a twenty six amino acid peptide, was chosen as the model antigen for the artificial antibody target[20]. Melittin, the major component of bee venom from *Apis mellifera*, has been well studied as a representative of cytolytic and hemolytic biotoxins that can act as a key virulence factor of infection diseases[21-23]. Melittin (600 nM) was added to the monomer solution prior to polymerization to synthesize melittin imprinted polymers (MIP) (FIG. 1a left). Control (non-imprinted) polymers (NIP) were prepared in an identical manner but in the absence of mellitin. Initiation was achieved by addition of ammonium persulfate and N,N,N',N'-tetramethylethylenediamine. Following polymerization, melittin and any unreacted monomers were removed by dialysis (FIG. 1a right). Particle size was measured by DLS and the yields of polymers in the library are given in table 1. The topographic image of MIP NPs (5% AAc 40% TBAm) was obtained by AFM. MIP NPs were well dispersed over a wide area of the mica surface (FIG. 2a, b) and the diameter of particles obtained from height profile was in a range of 30-40 nm (FIG. 2b insert). The size was comparable to that of IgM (FIG. 2c). The similarity in size could ensure that MIP NPs diffuse into extracellular matrixes and viscous body fluids such as mucus as well as blood and tissue fluids[5, 16].

Figure 3:
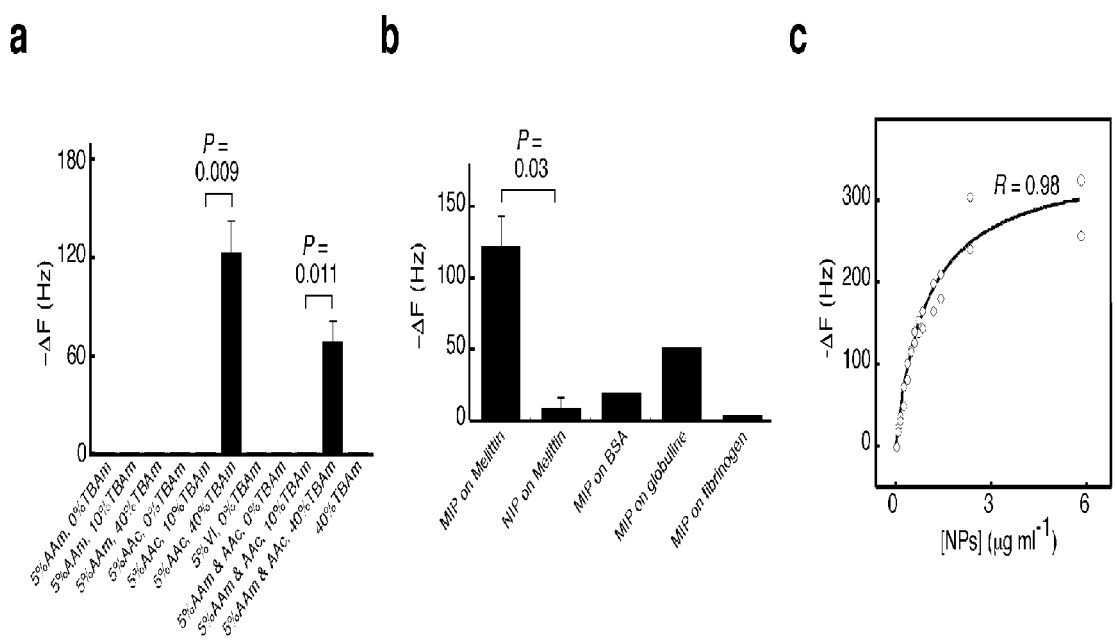
FIG. 3 shows the interaction between polymers and melittin or plasma proteins observed by QCM in 25° C. water with 6.9 μM of SDS. a. Screening of polymers that interact with melittin from polymer library by QCM. Data represent the mean frequency change±standard deviation (n=3) due to injection of 0.6 μg ml$^{-1}$ polymer solutions into melittin immobilized cells. b. Interaction of MIP or not imprinted (NIP) NPs (5 mol % AAc, 40 mol % TBAm, 2 mol % MBAm and 53 mol % NIPAm) on melittin or serum proteins immobilized QCM. c. A binding isotherm of the MIP NPs (5 mol % AAc, 40 mol % TBAm, 2 mol % MBAm and 53 mol % NIPAm) to melittin.

A 27 MHz quartz crystal microbalance (QCM) was used to assay interactions between the small library of MIPs and melittin (FIG. 3)[24]. Two optimum formulation of MIP NPs was achieved with 5% AAc 40% TBAm and 5% AAm 5% AAc 40% TBAm (FIG. 3a). Other formulations in the library had little affinity to melittin at this concentration range. Polymer NPs that were polymerized with 5% AAc and 40% TBAm without melittin (NIP) have a low affinity to melittin at the same concentration (FIG. 3b left two columns). Interactions between plasma proteins (albumin, fibrinogen and γ-globulin) and MIP NPs (5% AAc 40% TBAm) were also observed. The imprinted NPs had little or no interaction with albumin and fibrinogen (FIG. 3b); γ-globulin had a somewhat higher affinity to the MIP nanoparticle but less than melittin. MIP NP binding to a melittin immobilized QCM cell as a function of concentration is shown in FIG. 3c. A calculated apparent dissociation constant (K$_{d(app)}$) of 18-62 pM was obtained by nonlinear fitting of the binding plot to the Langmuir isotherm under an assumption that all particles in solution are homogeneous 40 nm spheres and polymer density is 0.08<ρ<0.27 (FIG. 3c)[18, 19, 25]. This dissociation constant is comparable to that of natural antibody (K$_d$=17 pM)[15]. From these results, it is concluded that the polymer NPs (5% AAc 40% TBAm) have been imprinted by melittin to produce complimentary binding sites. The binding sites are created during polymerization by the interactions between the developing polymer structure and melittin.

Figure 5:
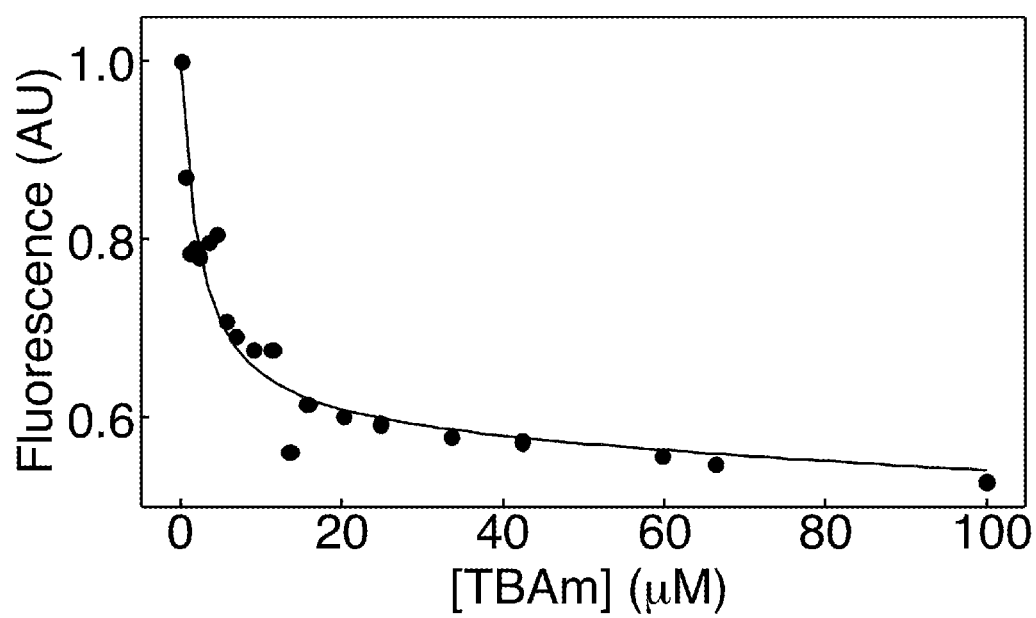
FIG. 5 shows fluorescence intensity of tryptophan on melittin quenched by TBAm.

Our QCM results demonstrate the importance of optimizing monomer combinations to achieve successful imprinting of target binding sites on polymer NPs. Such optimization can be performed for other target molecules by making various combinations of monomers as shown in Table 1. The target molecule, melittin, has 26 residues of which 6 are positively charged. The charged sites are from the N-terminus α-amino glycine, three ε-amino groups of lysines at positions 7, 21, and 23, and two guanidinium groups from arginines at positions 22 and 24. The sequence is amphiphilic, since six amino acids at the C-terminus of the peptide are hydrophilic, while the remainder have a high proportion of apolar residues. The successful monomer combination for melittin imprinting contains both 40% of hydrophobic monomers (TBAm) and 5% of negatively charged functional monomers (AAc). Other MIP NPs, even those MIP NPs containing 5% and AAc 10% TBAm, do not interact with melittin at the same concentration. Successful MIP NPs are capable of interacting with melittin by both electrostatic and hydrophobic interactions and enable melittin to be incorporated as a template into the polymerizing NPs with high efficiency. Several observations are consistent with this proposal. For example, the fluorescence of tryptophan in melittin is quenched in proportion to added TBAm. The diminution of fluorescence intensity occurs in the μM region (FIG. 5), indicating that at least one part of the target molecule interacts with TBAm monomers in the pre-polymerized mixture. In addition, a pre-polymerized monomer solution containing 40% TBAm became cloudy upon addition of melittin. Eventually, a TBAm feeding ratio of 40% was found to be optimum for the preparation of melittin imprinted NPs (copolymers synthesized with higher TBAm feed ratio (50%) forms aggregates after dialysis).

Figure 4:
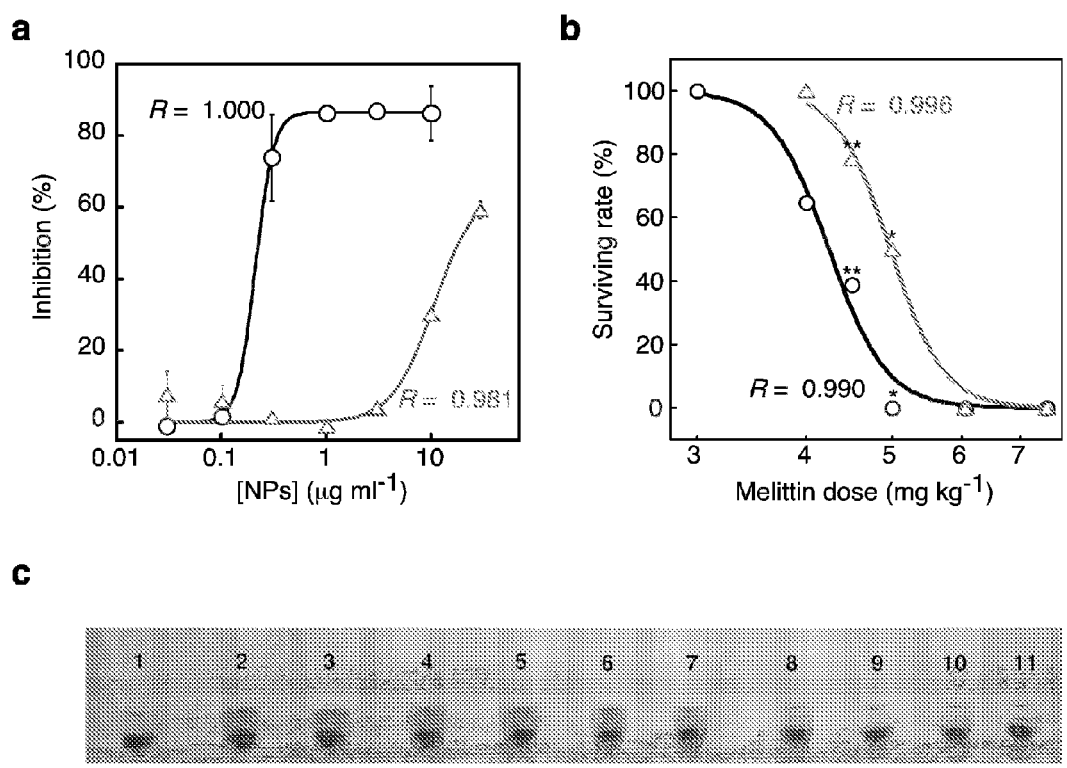
FIG. 4 shows neutralization of melittin activity by NPs (5 mol % AAc, 40 mol % TBAm, 2 mol % MBAm and 53 mol % NIPAm). a. Inhibition of melittin induced cytotoxicity in cultured cells by MIP/NIP (circles/triangles) NPs. The data represent the mean±SEM (n=4). b. Effect of MIP NPs on dose-dependent lethality of melittin in mice. Surviving rate of mice 24 hour after melittin injection with/without (triangles/circles) incubation with 9.4 mg kg$^{-1}$ MIP NPs were plotted (5≤n≤41). *P=0.016 and **P=0.003 were calculated by log-rank test. c. Photograph of centrifuged RBCs after 30 min incubation without melittin (tube 1), with melittin (tube 2), with melittin and 2.9, 8.8, 18, 29, 44, 73, 120, 180 and 210 μg ml$^{-1}$ MIP NPs (tube 3-11).

To estimate if MIP NPs have antibody-like function for neutralizing the bio-toxicity of the model antigen, the cytotoxicity of melittin was assayed with/without MIP NPs in vitro and in vivo. Inhibition of melittin induced cell death by MIP NPs (5% AAc 40% TBAm) in vitro was determined by the alamarBlue™ cell viability assay of HT-1080 human fibrosarcoma cells[26]. MIP NPs were found to inhibit the cytotoxicity of melittin over a range of concentrations (50% inhibition concentration; $IC_{50}$=0.212±0.005 μg m$l^{-1}$) (FIG. 4a). The data indicates that MIP NPs inhibit melittin toxicity in the presence of fetal bovine serum for 24 h. Non-imprinted nanoparticles (NIP NPs, 5% AAc 40% TBAm) can also inhibit melittin cytotoxicity at high concentration. However, $IC_{50}$ of NIP NPs (10.8±3.3 μg m$l^{-1}$) was almost 50 times higher than that of MIP NPs.

The in vitro result suggests that the artificial MIP NP antibody-antigen affinity is sufficiently strong to neutralize melittin's toxicity rather than exchange with serum proteins in vivo. The neutralization activity of MIP NPs (5% AAc 40% TBAm) in vivo was established by observing the survival rate of mice 24 h after intravenous injection of melittin[27]. A dose of 5.0 mg k$g^{-1}$ of melittin results in 100% mortality within 1 h. When imprinted NPs were injected along with a dose of 5.0 mg k$g^{-1}$ melittin, 50% of mice survived to 24 h (p value is 0.016; see FIG. 6). The 50% lethal dose ($LD_{50}$) of melittin (4.24±0.07 mg k$g^{-1}$) was improved by pre-incubation with MIP NPs to 4.96±0.05 mg k$g^1$ (FIG. 4b). This improvement suggests 0.72 mg k$g^{-1}$ of melittin was neutralized by 9.4 mg k$g^{-1}$ MIP NPs. The apparent binding capacity of the MIP NPs was calculated to be 27 μmol k$g^{-1}$ which is twice of that of natural antibodies (2 target molecules per 150 kDa single IgG=13 μmol $g^{-1}$). Importantly, at the quantities injected, obvious side effects due to polymer NPs for at least one week were not detected.

Figure 6:
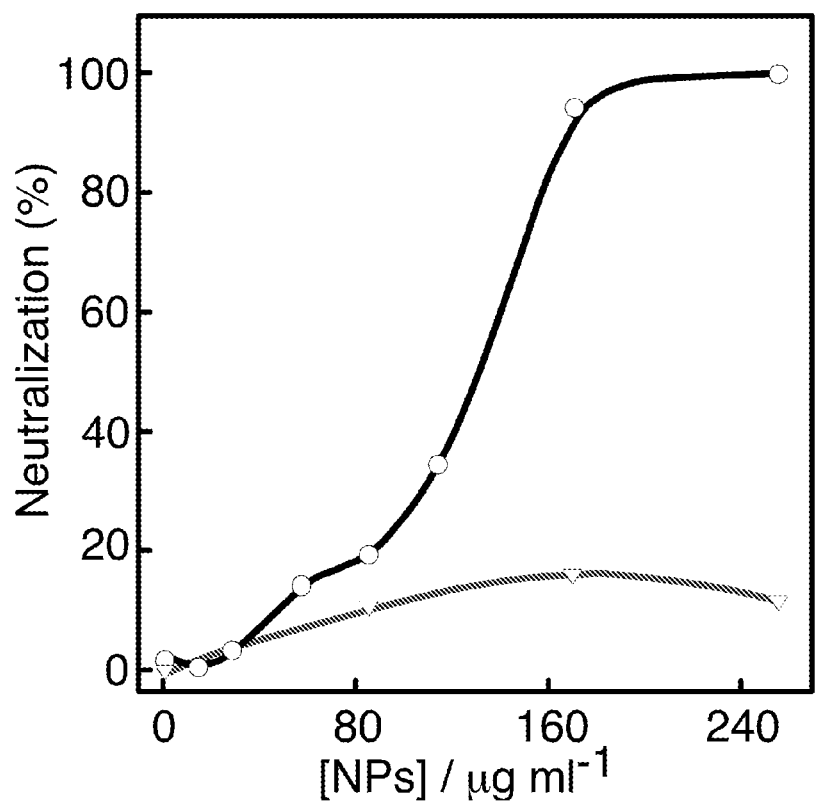
FIG. 6 shows inhibition efficiency of hemolytic activity of melittin (white circles) and α-toxin (white triangles) by melittin imprinted NPs.

Further demonstration of the in vitro hemolytic activity of MIP NPs was obtained from a neutralization assay using red blood cells (FIG. 4c)[28]. Without MIP NPs, the supernatant of a centrifuged solution of red blood cells' turned red after incubation with melittin. The solution color arises from release of hemoglobin induced by the pore formation by melittin. (FIG. 4c, tube 1-2). However upon incubation with melittin, solutions become increasingly transparent as more MIP NPs were added to the solution (FIG. 4c, tube 2-11). The neutralization efficiency of melittin's hemolytic activity was calculated to be 11 μmol $g^{-1}$ from the neutralization curve (FIG. 6). This value is comparable to that obtained by the in vivo study (FIG. 4b). The neutralization activity of melittin imprinted NPs for a different hemolytic toxin, α-Toxin from Staphylococcus aureus, was also determined[29]. Significantly, it was found that the melittin imprinted NPs were antigen specific, that is, they were ineffective in inhibiting the hemolytic activity of α-toxin (FIG. 6).

In summary, optimum nanoparticle formulation (for the melittin target) was selected by a small combinatorial library of NIPAm based co-polymers to prepare molecularly imprinted polymer NPs against the peptide toxin melittin. Optimization of the composition of functional monomers that can interact with target molecules was used for successful imprinting. Such optimization can be used for different target molecules using methods, such at those discussed above for melittin. The imprinted NPs are capable of capturing the target molecule selectively and neutralizing its activity in vitro and in vivo. Its binding affinity, capacity and size of particles are similar to that of natural antibodies. Because, these "artificial antibodies" are not biodegradable and are chemically more stable than protein antibodies, they should remain longer in enzymatic environment such as intestines, stomach or mucosa as well as body fluids without being digested by proteases. Furthermore, because they can be rapidly synthesized for low cost, it would be easy to mass-produce them in a relatively short period of time in response to emergencies[2-3].

Example 2

Imprinted Nanoparticles that Bind Antibodies

This examples describes methods that could be used to generate imprinted nanoparticles that bind the Fc region of antibodies and the use of these nanoparticles to purify a monoclonal antibody such that it could be used therapeutically.

As a first method, one could employ the Fc region or IgG as an imprinting molecule. In this approach, one could dissolve the Fc region or IgG in polymerization solution with combinations of functional monomers with or without surfactant to form well dispersed nanoparticles. Then resulting solution can be purified by dialysis, chromatography or extraction. Extracted polymer libraries can be examined by QCM, SPR, SDS PAGE or ELISA to quantify affinity to a number of proteins as well as Fc region and IgG. From affinity result, one could identify the best combination of monomers to get highly specific and high affinity nanoparticles. One could then categorize the types of interactions that are necessary to get high affinity. Under the obtained combination of categorized interaction, one could tune monomer structure and feed ratio to optimize the binding properties. One could also examine the size and stability of nanoparticles by DLS, AFM, SEM, SEC, Mass spectra.

One could also optimize monomer concentration, reaction temperature, structure of surfactant, concentration of surfactant, concentration and structure of initiator and catalyst to get best performance.

In a particular methods, one could use exposed peptide sequences (epitopes) on Fc region as imprinting molecules.

Those relatively short polypeptide are less likely to be aggregated during polymerization. One could identify exposed epitopes of IgG on the conserved Fc domain of the antibody IgG (PDB ID; ligt) as preferably target molecules. The epitopes are comprised of exposed (loops or bulges) hydrophilic regions on the B chain of the Fc domain. Three exemplary sequences that one might employ in the B chain are: 302-318 (HTAQTQTHREDYNST, SEQ ID NO:1), aa353-aa369 (15 aa) RTISKPKGSVRAPQV, SEQ ID NO:2, and aa408-aa425 (15 aa) NNGKTELNYKNTEPV (SEQ ID NO:3). In addition the C-terminus, aa466-474 (HHTTKSFSR, SEQ ID NO:4) of the B chain, is also exposed and hydrophilic and could be employed. In certain embodiments, one could functionalize both ends of the target peptide with PEG groups. This aids in orienting the hydrophobi domain at the surface of the polymerizing particle.

Optimized MIP NPs can be immobilized on a solid support by well established method such as amine coupling method. The amine coupling method is well established methods to immobilize proteins on a solid support such as glass or polymer via amine group on the surface of protein. One can incorporate amine groups on the nanoparticles by copolymerize monomers such as N-(3-aminopropyl)acrylamide.

Example 3

Imprinted Nanoparticles for Elimination of Polypeptides

This examples describes methods that could be used to generate imprinted nanoparticles that bind PMSα peptides, α-hemolysin, anthrax neurotoxins, botulinum neurotoxins, LPS, envelope proteins of HIV, HHV, influenzavirus and hepatitis viruses.

As an initial target, one could use epitopes of the *Staphylococcus aureus* α toxin to generate nanoparticles capable of neutralizing the entire protein. A library of synthetic polymer nanoparticles could be created with various combinations of functional monomers and screened against their tendency to aggregate. These particles could then be characterized with DLS for particle size, Z-potential to evaluate surface charge, and lyophilization to measure particle mass and particle yield. The final evaluation could be a screening of hemolytic activity of the material itself and its ability to neutralize a toxin without being imprinted. One could also synthesize epitope imprinted particles and evaluate their neutralization activity using a hemolysis test quantified with UV-VIS. A subsequent binding assay with QCM could show which of the epitope and monomer combinations produce the highest affinities. This process could be iterated and proceed concurrently as necessary. One could also conduct tests with AFM, SEM, and SLS to characterize the final products.

Exemplary monomers that could be used in various combinations include the following: hydrophobic monomers (N-isopropyl acrylamide and t-butyl acrylaamide), hydrogen-bonding monomer (acrylamide), positively charged monomer (vinyl imidazole), negatively charged monomer (aclylic acid), aromatic monomer (N-dansylated acrylamide), and the cross-linking monomer (N,N'-ethylene bisacrilamide). The choice of which of these to use could be based on screening done, and optimal proportions could be determined in an iterative round.

*Staphylococcus aureus* α toxin (33 kDa protein) may be used as a target as it has similarities to melittin, in that it is pore forming and has hemolytic activity. It also has similarities to toxins listed by the NIAID in Categories A-B, and the stem domain (FIG. 1C) of the protomer, the form that is found in solution, is a positively charged, hydrophobic sequence. Nanoparticles generated to toxins, such as *S. aureous* toxin, may be used to therapeutically treat a subject.

REFERENCES

1. Adams, P. G. & Weiner, M. L. Monoclonal antibody therapy of cancer. *Nat. Biotech.*, 23, 1147-1157 (2005).
2. Casadevall, A. Passive antibody administration (immediate immunity) as a specific defense against biological weapons. *Emerg. Infect. Disease.*, 8, 833-841 (2002).
3. Casadevall, A. Serum therapy revisited: Animal models of infection and development of passive antibody therapy. *Antimicrob. Agents Chemother.*, 38, 1695-1702 (1994).
4. Duncan, R. The dawning era of polymer therapeutics. *Nature Rev. Drug. Discov.* 2, 347-360 (2003).
5. Rothenfluh O, D. A., Bermudez, H., O'neil, C. P. & Hubbell, J. A. Biofunctional polymer nanoparticles for intra-articular targeting and retention in cartilage. *Nature Mater.* 7, 248-254 (2008).
6. Wulff, G. & Sarhan, A. Use of polymers with enzyme-analogous structures for the resolution of racemates. *Angew. Chem. Int. Edn. Engl.* 11, 341-343 (1972).
7. Mosbach, K. The promise of molecular imprinting. *Scientific American* 295, 86-91 (2006).
8. Yan, M. & Ramström, O. *Molecularly imprinted materials, science and technology* (Marcel Dekker, 2005).
9. Hart, B. R. & Shea, K. J. Synthetic peptide receptors: molecularly imprinted polymers for the recognition of peptides using peptide-metal interactions. *J. Am. Chem. Soc.* 123, 2072-2073 (2001).
10. Rachkov, A. Minoura, N. & Shimizu, T. Peptide separation using molecularly imprinted polymer prepared by epitope approach. *Anal. Sci.* 17, 609-612 (2001).
11. Hansen, E. D. Recent developments in the molecular imprinting of proteins. *Biomaterials* 28, 4178-4191 (2007).
12. Nishino, H, Huang, C.-S. & Shea, K. J. Selective Protein Capture by Epitope Imprinting, *Angew. Chem. Int. Ed.* 2006, 45, 2392-2396.
13. Li, Y. Yang, H. H. You, Q. H. Zhuang, Z. X. & Wang, X. R. Protein recognition via surface molecularly imprinted polymer nanowires. *Anal. Chem.* 78, 317-320 (2006).
14. Tan, C. J. & Tong, Y. W. The effect of protein structural conformation on nanoparticle molecular imprinting of ribonuclease A using miniemulsion polymerization. *Langmuir.* 23, 2722-2730 (2007).
15. Grünigen, R. V. & Schneider, C. H. Antigenic structure of the hexacosapeptide melittin: evidence for three determinants, one with a helical conformation. *Immunology* 66, 339-342 (1989).
16. Olmsted, S. S. et al. Diffusion of macromolecules and virus-like particles in human cervical muscus. *Biophys. J.* 81, 1930-1937 (2001).
17. Rosenqvist, E. Jossang, T. & Feder, J. Thermal properties of human IgG. *Mol. Immun.* 24, 495-501 (1987).
18. Debord, J. D. & Lyon, L. A. Synthesis and characterization of pH-responsible copolymer microgels with tunable volume phase transition temperatures. *Langmuir* 19, 7662-7664 (2003).
19. Ogawa, K., Nakayama A. & Kokufuta, E. Preparation and characterization of thermosensitive polyampholyte nanogels. *Langmuir* 19, 3178-3184 (2003).
20. Habermann, E. Bee and wasp venoms. *Science* 177, 314-322 (1972).

21. Wang, R. et al. Identification of novel cytolytic peptides as key virulence determinants for community-associated MRSA. *Nature Med.* 13, 1510-1514 (2007).
22. Bechinger, B. Structure and function of channel-forming peptides: Maganins, cecropins, melittin and alamethicin. *J. Membrane Biol.* 156, 197-211 (1997).
23. Britt, A. M., Burkhart, K. K. & Billingsley, M. L. Reversal of toxicity using avidin-based hemoperfusion: A model system in rats using biotinylated melittin. *Pharmacology.* 50, 307-312 (1995).
24. Hoshino, Y., Kawasaki, T. & Okahata, Y. Effect of ultrasound on DNA polymerase reactions: monitoring on a 27-MHz quartz crystal microbalance. *Biomacromol.* 7, 682-685 (2006).
25. Ebara, Y. & Okahata, Y. A kinetic study of concanavalin A binding to glycolipid monolayers by using a quartz-crystal microbalance. *J. Am. Chem. Soc.* 116, 11209-11212 (1994).
26. Ahmed, S. A., Gogal, R. M. J. & Walsh, J. E. A new Rapid and simple non-radioactive assay to monitor and determine the proliferation of lymphocytes: An alternative to H3-thymidine incorporation assay. *J. Immunol. Methods* 170, 211-224 (1994).
27. Habermann, E. & Zeuner, G. Comparative studies of native and synthetic melittins. *Naunyn-schmiedebergs Arch. Pharmak.* 270, 1-9 (1971)
28. Oren, Z. & Shai, Y. Selective lysis of bacteria but not mammalian cells by diastereomers of melittin: Structure-function study. *Biochemistry* 36, 1826-1835 (1997).
29. Wardenburg, B. J. et al. Poring over pores: α-hemolysin and Panton-Valentine leukocidin in *Staphylococcus aureus* pneumonia. *Nature Med.* 13, 1405-1406 (2007).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry and molecular biology or related fields are intended to be within the scope of the following claims.

We claim:

1. A method of making imprinted polymer nanoparticles comprising:
    a) combining at least one type of monomers, a cross-linking agent, and target molecules in an aqueous medium to generate a reaction mixture, wherein said at least one type of monomer comprises N-tert-butylacrylamide (TBAm) momomers; and
    b) incubating said reaction mixture under polymerization conditions such that imprinted polymer nanoparticles are generated that are specific for said target molecules.

2. The method of claim 1, wherein said at least one type of monomer further comprises acrylic acid monomers.

3. The method of claim 1, wherein said reaction mixture further comprises N-isopropylacrylamide (NIPAm) monomers.

4. The method of claim 1, wherein said target molecules are proteins.

5. The method of claim 1, wherein said target molecules are toxins.

6. The method of claim 1, wherein said target molecules are polysaccharides.

7. The method of claim 1, wherein said reaction mixture further comprises an ionic surfactant.

8. The method of claim 7, wherein said ionic surfactant comprises sodium dodecyl sulfate.

9. The method of claim 1, wherein said crosslinking agent comprises N,N'-methylenebis(acrylamide).

10. The method of claim 1, wherein said at least one type of monomer further comprises acrylamide monomers.

11. The method of claim 1, wherein said crosslinking agent comprises N,N'-methylenebis(acrylamide) and wherein said reaction mixture further comprises N-isopropylacrylamide (NIPAm) monomers.

12. The method of claim 11, wherein said at least one type of monomer further comprises acrylic acid monomers.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

His Thr Ala Gln Thr Gln Thr His Arg Glu Asp Tyr Asn Ser Thr
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Arg Thr Ile Ser Lys Pro Lys Gly Ser Val Arg Ala Pro Gln Val
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Asn Asn Gly Lys Thr Glu Leu Asn Tyr Lys Asn Thr Glu Pro Val
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4
```

```
His His Thr Thr Lys Ser Phe Ser Arg
1               5

<210> SEQ ID NO 5
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: The residue at this position is linked to NH2.

<400> SEQUENCE: 5

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25
```